US007425335B2

(12) United States Patent
Gore et al.

(10) Patent No.: US 7,425,335 B2
(45) Date of Patent: Sep. 16, 2008

(54) CHIMERIC T HELPER-B CELL PEPTIDE VACCINE FOR JAPANESE ENCEPHALITIS VIRUS

(75) Inventors: M. M. Gore, Pune (IN); Ashok Kolaskar, Pune (IN); S. S. Dewasthaly, Pune (IN); Urmila D. Kulkarani-Kale, Pune (IN); Sangeeta Sawant, Pune (IN)

(73) Assignees: The Secretary Department of Biotechnology, New Delhi (IN); National Institute of Virology, Pune (IN); University of Pune, Pune (IN)

( * ) Notice: Subject to any disclaimer, the term of this patent is extended or adjusted under 35 U.S.C. 154(b) by 92 days.

(21) Appl. No.: 10/250,468

(22) PCT Filed: Jan. 4, 2002

(86) PCT No.: PCT/IN02/00003

§ 371 (c)(1),
(2), (4) Date: Nov. 4, 2003

(87) PCT Pub. No.: WO02/053182

PCT Pub. Date: Jul. 11, 2002

(65) Prior Publication Data

US 2004/0076634 A1 Apr. 22, 2004

(30) Foreign Application Priority Data

Jan. 5, 2001 (IN) ............................... 13/DEL/01

(51) Int. Cl.
*A61K 39/12* (2006.01)

(52) U.S. Cl. ................................................... 424/186.1

(58) Field of Classification Search .............. 424/130.1, 424/139.1, 184.1, 185.1, 192.1; 530/300
See application file for complete search history.

(56) References Cited

FOREIGN PATENT DOCUMENTS

WO WO 88/03032 A1 5/1988

OTHER PUBLICATIONS

Tam et al. Incorporation of T and B epitopes of the circumsporozoite protein in a chemically defined synthetic vaccine against malaria. J. Exp. Med. 1990 171: 299-306.*

Fields Virology, 4th edition, Lippincott Williams & Wilkins, 2001, pp. 437-438.*

Saini et al. A Japanese Encephalitis Virus Peptide Present on Johnson Grass Mosaic Virus-Like Particles Induces Virus-Neutralizing Antibodies and Protects Mice against Lethal Challenge. Journal of Virology, Mar. 2003; 77(6): 3487-3494.*

Kutubuddin, M. et al., "Analysis of computer-predicted antibody inducing epitope on Japanese encephalitis virus", Acta Virol., (Engl. Ed), (1993) 37 (6), pp. 417-428, abstract.

Roehring, J.T. et al., "Enhancement of the antibody response to flavivirus B-cell epitopes by using homologous or heterologous T-cell epitopes", J. Virol. (1992), 66(6), pp. 3385-3390, abstract.

* cited by examiner

*Primary Examiner*—Bruce Campbell
*Assistant Examiner*—Emily M. Le
(74) *Attorney, Agent, or Firm*—Venable LLP; Catherine M. Voorhees; Nancy J. Axelrod

(57) ABSTRACT

A vaccine composition for humans and animals against Japanese encephalitis virus infection is a composition which comprises a chimeric synthetic peptide selected from envelope glycoprotein consisting of amino acids Egp 149-SENHGNYSAQVGASQ-163 (SEQ ID NO:1) AND Egp 429-SIGGVFNSIGKAVHQVFG-446 (SEQ ID NO:2) of Japanese encephalitis virus envelope glycoprotein, present in an amount sufficient to induce protective immunity against Japanese encephalitis virus infection.

7 Claims, 4 Drawing Sheets

SEQUENCE LISTING

<160> NUMBER OF SEQ ID NOS: 86

<210> SEQ ID NO 1
<211> LENGTH: 15
<212> TYPE: PRT
<213> ORGANISM: Japanese encephalitis virus

<400> SEQUENCE: 1

Ser Glu Asn His Gly Asn Tyr Ser Ala Gln Val Gly Ala Ser Gln
1               5                   10                  15

<210> SEQ ID NO 2
<211> LENGTH: 18
<212> TYPE: PRT
<213> ORGANISM: Japanese encephalitis virus

<400> SEQUENCE: 2

Ser Ile Gly Gly Val Phe Asn Ser Ile Gly Lys Ala Val His Gln Val
1               5                   10                  15

Phe Gly

<210> SEQ ID NO 3
<211> LENGTH: 19
<212> TYPE: PRT
<213> ORGANISM: Japanese encephalitis virus

<400> SEQUENCE: 3

Ser Glu Asn His Gly Asn Tyr Ser Ala Gln Val Gly Ala Ser Gln Ala
1               5                   10                  15

Ala Lys Phe

<210> SEQ ID NO 4
<211> LENGTH: 12
<212> TYPE: PRT
<213> ORGANISM: Japanese encephalitis virus

<400> SEQUENCE: 4

Pro Thr Leu Asp Val Arg Met Ile Asn Ile Glu Ala
1               5                   10

<210> SEQ ID NO 5
<211> LENGTH: 11
<212> TYPE: PRT
<213> ORGANISM: Japanese encephalitis virus

<400> SEQUENCE: 5

Glu Tyr Ser Ser Ser Val Lys Leu Thr Ser Gly
1               5                   10

<210> SEQ ID NO 6
<211> LENGTH: 16
<212> TYPE: PRT
<213> ORGANISM: Japanese encephalitis virus

<400> SEQUENCE: 6

Thr Trp Val Asp Leu Val Leu Glu Gly Asp Ser Cys Leu Thr Ile Met
1               5                   10                  15

<210> SEQ ID NO 7
<211> LENGTH: 7
<212> TYPE: PRT
<213> ORGANISM: Japanese encephalitis virus

<400> SEQUENCE: 7

Thr Leu Asp Val Arg Met Ile
 1               5

<210> SEQ ID NO 8
<211> LENGTH: 28
<212> TYPE: PRT
<213> ORGANISM: Japanese encephalitis virus

<400> SEQUENCE: 8

Ile Glu Ala Val Gln Leu Ala Glu Val Arg Ser Tyr Cys Tyr His Ala
 1               5                  10                  15

Ser Val Thr Asp Ile Ser Thr Val Ala Arg Cys Pro
            20                  25

<210> SEQ ID NO 9
<211> LENGTH: 18
<212> TYPE: PRT
<213> ORGANISM: Japanese encephalitis virus

<400> SEQUENCE: 9

Cys Pro Thr Thr Gly Glu Ala His Asn Glu Lys Arg Ala Asp Ser Ser
 1               5                  10                  15

Tyr Val

<210> SEQ ID NO 10
<211> LENGTH: 8
<212> TYPE: PRT
<213> ORGANISM: Japanese encephalitis virus

<400> SEQUENCE: 10

Ser Ser Tyr Val Cys Lys Gln Gly
 1               5

<210> SEQ ID NO 11
<211> LENGTH: 12
<212> TYPE: PRT
<213> ORGANISM: Japanese encephalitis virus

<400> SEQUENCE: 11

Ile Asp Thr Cys Ala Lys Phe Ser Cys Thr Ser Lys
 1               5                  10

<210> SEQ ID NO 12
<211> LENGTH: 26
<212> TYPE: PRT
<213> ORGANISM: Japanese encephalitis virus

<400> SEQUENCE: 12

Tyr Ser Ala Gln Val Gly Ala Ser Gln Ala Ala Lys Phe Thr Val Thr
 1               5                  10                  15

Pro Asn Ala Pro Ser Ile Thr Leu Lys Leu
            20                  25

<210> SEQ ID NO 13
<211> LENGTH: 11
<212> TYPE: PRT
<213> ORGANISM: Japanese encephalitis virus

<400> SEQUENCE: 13

Thr Thr Thr Ser Glu Asn His Gly Asn Tyr Ser
 1               5                  10

```
<210> SEQ ID NO 14
<211> LENGTH: 28
<212> TYPE: PRT
<213> ORGANISM: Japanese encephalitis virus

<400> SEQUENCE: 14

Tyr Ser Ala Gln Val Gly Ala Ser Gln Ala Ala Lys Phe Thr Val Thr
 1               5                  10                  15

Pro Asn Ala Pro Ser Ile Thr Leu Lys Leu Gly Asp
            20                  25

<210> SEQ ID NO 15
<211> LENGTH: 7
<212> TYPE: PRT
<213> ORGANISM: Japanese encephalitis virus

<400> SEQUENCE: 15

Glu Val Thr Leu Asp Cys Glu
 1               5

<210> SEQ ID NO 16
<211> LENGTH: 8
<212> TYPE: PRT
<213> ORGANISM: Japanese encephalitis virus

<400> SEQUENCE: 16

Glu Ala Phe Tyr Val Met Thr Val
 1               5

<210> SEQ ID NO 17
<211> LENGTH: 9
<212> TYPE: PRT
<213> ORGANISM: Japanese encephalitis virus

<400> SEQUENCE: 17

Ser Lys Ser Phe Leu Val His Arg Glu
 1               5

<210> SEQ ID NO 18
<211> LENGTH: 12
<212> TYPE: PRT
<213> ORGANISM: Japanese encephalitis virus

<400> SEQUENCE: 18

Trp Thr Pro Pro Ser Ser Thr Ala Trp Arg Asn Arg
 1               5                  10

<210> SEQ ID NO 19
<211> LENGTH: 7
<212> TYPE: PRT
<213> ORGANISM: Japanese encephalitis virus

<400> SEQUENCE: 19

Leu His Gln Ala Leu Ala Gly
 1               5

<210> SEQ ID NO 20
<211> LENGTH: 9
<212> TYPE: PRT
<213> ORGANISM: Japanese encephalitis virus

<400> SEQUENCE: 20

Phe Glu Glu Ala His Ala Thr Lys Gln
```

```
                              1               5

<210> SEQ ID NO 21
<211> LENGTH: 18
<212> TYPE: PRT
<213> ORGANISM: Japanese encephalitis virus

<400> SEQUENCE: 21

Glu Tyr Ser Ser Ser Val Lys Leu Thr Ser Gly His Leu Lys Cys Arg
 1               5                  10                  15

Leu Lys

<210> SEQ ID NO 22
<211> LENGTH: 7
<212> TYPE: PRT
<213> ORGANISM: Japanese encephalitis virus

<400> SEQUENCE: 22

Asp Lys Leu Ala Leu Lys Gly
 1               5

<210> SEQ ID NO 23
<211> LENGTH: 11
<212> TYPE: PRT
<213> ORGANISM: Japanese encephalitis virus

<400> SEQUENCE: 23

Phe Ala Phe Ala Lys Asn Pro Ala Asp Thr Gly
 1               5                  10

<210> SEQ ID NO 24
<211> LENGTH: 10
<212> TYPE: PRT
<213> ORGANISM: Japanese encephalitis virus

<400> SEQUENCE: 24

Gly Thr Val Val Ile Glu Leu Ser Tyr Ser
 1               5                  10

<210> SEQ ID NO 25
<211> LENGTH: 8
<212> TYPE: PRT
<213> ORGANISM: Japanese encephalitis virus

<400> SEQUENCE: 25

Ser Tyr Ser Gly Ser Asp Gly Pro
 1               5

<210> SEQ ID NO 26
<211> LENGTH: 8
<212> TYPE: PRT
<213> ORGANISM: Japanese encephalitis virus

<400> SEQUENCE: 26

Val Gly Arg Leu Val Thr Val Asn
 1               5

<210> SEQ ID NO 27
<211> LENGTH: 9
<212> TYPE: PRT
<213> ORGANISM: Japanese encephalitis virus

<400> SEQUENCE: 27

Asn Ser Lys Val Leu Val Glu Met Glu
```

```
<210> SEQ ID NO 28
<211> LENGTH: 7
<212> TYPE: PRT
<213> ORGANISM: Japanese encephalitis virus

<400> SEQUENCE: 28

Ala Thr Ser Ser Ala Asn Ser
 1               5

<210> SEQ ID NO 29
<211> LENGTH: 9
<212> TYPE: PRT
<213> ORGANISM: Japanese encephalitis virus

<400> SEQUENCE: 29

Gly Asp Ser Tyr Ile Val Val Gly Arg
 1               5

<210> SEQ ID NO 30
<211> LENGTH: 11
<212> TYPE: PRT
<213> ORGANISM: Japanese encephalitis virus

<400> SEQUENCE: 30

Thr Leu Asp Val Arg Met Ile Asn Ile Glu Ala
 1               5                   10

<210> SEQ ID NO 31
<211> LENGTH: 13
<212> TYPE: PRT
<213> ORGANISM: Japanese encephalitis virus

<400> SEQUENCE: 31

Ile Val Val Glu Tyr Ser Ser Ser Val Lys Leu Thr Ser
 1               5                   10

<210> SEQ ID NO 32
<211> LENGTH: 10
<212> TYPE: PRT
<213> ORGANISM: Japanese encephalitis virus

<400> SEQUENCE: 32

Pro Thr Leu Asp Val Arg Met Ile Asn Ile
 1               5                   10

<210> SEQ ID NO 33
<211> LENGTH: 13
<212> TYPE: PRT
<213> ORGANISM: Japanese encephalitis virus

<400> SEQUENCE: 33

Ala Ile Val Val Glu Tyr Ser Ser Ser Val Lys Leu Thr
 1               5                   10

<210> SEQ ID NO 34
<211> LENGTH: 17
<212> TYPE: PRT
<213> ORGANISM: Japanese encephalitis virus

<400> SEQUENCE: 34

Asn His Gly Asn Tyr Ser Ala Gln Val Gly Ala Ser Gln Ala Ala Lys
 1               5                   10                  15
```

Phe

<210> SEQ ID NO 35
<211> LENGTH: 8
<212> TYPE: PRT
<213> ORGANISM: Japanese encephalitis virus

<400> SEQUENCE: 35

Ile Met Ala Asn Asp Lys Pro Thr
 1               5

<210> SEQ ID NO 36
<211> LENGTH: 8
<212> TYPE: PRT
<213> ORGANISM: Japanese encephalitis virus

<400> SEQUENCE: 36

Ala Asn Asp Lys Pro Thr Leu Asp
 1               5

<210> SEQ ID NO 37
<211> LENGTH: 8
<212> TYPE: PRT
<213> ORGANISM: Japanese encephalitis virus

<400> SEQUENCE: 37

Asp Lys Pro Thr Leu Asp Val Arg
 1               5

<210> SEQ ID NO 38
<211> LENGTH: 8
<212> TYPE: PRT
<213> ORGANISM: Japanese encephalitis virus

<400> SEQUENCE: 38

Pro Thr Leu Asp Val Arg Met Ile
 1               5

<210> SEQ ID NO 39
<211> LENGTH: 8
<212> TYPE: PRT
<213> ORGANISM: Japanese encephalitis virus

<400> SEQUENCE: 39

Thr Leu Asp Val Arg Met Ile Asn
 1               5

<210> SEQ ID NO 40
<211> LENGTH: 8
<212> TYPE: PRT
<213> ORGANISM: Japanese encephalitis virus

<400> SEQUENCE: 40

Leu Asp Val Arg Met Ile Asn Ile
 1               5

<210> SEQ ID NO 41
<211> LENGTH: 8
<212> TYPE: PRT
<213> ORGANISM: Japanese encephalitis virus

<400> SEQUENCE: 41

Asp Val Arg Met Ile Asn Ile Glu
 1               5

<210> SEQ ID NO 42
<211> LENGTH: 8
<212> TYPE: PRT
<213> ORGANISM: Japanese encephalitis virus

<400> SEQUENCE: 42

Val Arg Met Ile Asn Ile Glu Ala
 1               5

<210> SEQ ID NO 43
<211> LENGTH: 8
<212> TYPE: PRT
<213> ORGANISM: Japanese encephalitis virus

<400> SEQUENCE: 43

Met Ile Asn Ile Glu Ala Ser Gln
 1               5

<210> SEQ ID NO 44
<211> LENGTH: 8
<212> TYPE: PRT
<213> ORGANISM: Japanese encephalitis virus

<400> SEQUENCE: 44

Asn Ile Glu Ala Ser Gln Leu Ala
 1               5

<210> SEQ ID NO 45
<211> LENGTH: 9
<212> TYPE: PRT
<213> ORGANISM: Japanese encephalitis virus

<400> SEQUENCE: 45

Tyr Ser Ala Gln Val Gly Ala Ser Gln
 1               5

<210> SEQ ID NO 46
<211> LENGTH: 13
<212> TYPE: PRT
<213> ORGANISM: Japanese encephalitis virus

<400> SEQUENCE: 46

Asn His Gly Asn Tyr Ser Ala Gln Val Gly Ala Ser Gln
 1               5                   10

<210> SEQ ID NO 47
<211> LENGTH: 13
<212> TYPE: PRT
<213> ORGANISM: Japanese encephalitis virus

<400> SEQUENCE: 47

Tyr Ser Ala Gln Val Gly Ala Ser Gln Ala Ala Lys Phe
 1               5                   10

<210> SEQ ID NO 48
<211> LENGTH: 8
<212> TYPE: PRT
<213> ORGANISM: Japanese encephalitis virus

<400> SEQUENCE: 48

Ala Ile Val Val Glu Tyr Ser Ser
 1               5

<210> SEQ ID NO 49

```
<211> LENGTH: 8
<212> TYPE: PRT
<213> ORGANISM: Japanese encephalitis virus

<400> SEQUENCE: 49

Ile Val Val Glu Tyr Ser Ser Ser
 1               5

<210> SEQ ID NO 50
<211> LENGTH: 8
<212> TYPE: PRT
<213> ORGANISM: Japanese encephalitis virus

<400> SEQUENCE: 50

Val Val Glu Tyr Ser Ser Ser Val
 1               5

<210> SEQ ID NO 51
<211> LENGTH: 8
<212> TYPE: PRT
<213> ORGANISM: Japanese encephalitis virus

<400> SEQUENCE: 51

Val Glu Tyr Ser Ser Ser Val Lys
 1               5

<210> SEQ ID NO 52
<211> LENGTH: 8
<212> TYPE: PRT
<213> ORGANISM: Japanese encephalitis virus

<400> SEQUENCE: 52

Glu Tyr Ser Ser Ser Val Lys Leu
 1               5

<210> SEQ ID NO 53
<211> LENGTH: 8
<212> TYPE: PRT
<213> ORGANISM: Japanese encephalitis virus

<400> SEQUENCE: 53

Tyr Ser Ser Ser Val Lys Leu Thr
 1               5

<210> SEQ ID NO 54
<211> LENGTH: 8
<212> TYPE: PRT
<213> ORGANISM: Japanese encephalitis virus

<400> SEQUENCE: 54

Ser Ser Ser Val Lys Leu Thr Ser
 1               5

<210> SEQ ID NO 55
<211> LENGTH: 8
<212> TYPE: PRT
<213> ORGANISM: Japanese encephalitis virus

<400> SEQUENCE: 55

Ser Ser Val Lys Leu Thr Ser Gly
 1               5

<210> SEQ ID NO 56
<211> LENGTH: 13
<212> TYPE: PRT
```

-continued

<213> ORGANISM: Japanese encephalitis virus

<400> SEQUENCE: 56

Thr Leu Asp Val Arg Met Ile Asn Ile Glu Ala Ser Gln
1               5                   10

<210> SEQ ID NO 57
<211> LENGTH: 16
<212> TYPE: PRT
<213> ORGANISM: Japanese encephalitis virus

<400> SEQUENCE: 57

Ser Glu Asn His Gly Asn Tyr Ser Ala Gln Val Gly Ala Ser Gln Ala
1               5                   10                  15

<210> SEQ ID NO 58
<211> LENGTH: 9
<212> TYPE: PRT
<213> ORGANISM: Japanese encephalitis virus

<400> SEQUENCE: 58

Tyr Ser Ala Gln Val Gly Ala Ser Gln
1               5

<210> SEQ ID NO 59
<211> LENGTH: 13
<212> TYPE: PRT
<213> ORGANISM: Japanese encephalitis virus

<400> SEQUENCE: 59

Asn His Gly Asn Tyr Ser Ala Gln Val Gly Ala Ser Gln
1               5                   10

<210> SEQ ID NO 60
<211> LENGTH: 15
<212> TYPE: PRT
<213> ORGANISM: Japanese encephalitis virus

<400> SEQUENCE: 60

Ser Glu Asn His Gly Asn Tyr Ser Ala Gln Val Gly Ala Ser Gln
1               5                   10                  15

<210> SEQ ID NO 61
<211> LENGTH: 13
<212> TYPE: PRT
<213> ORGANISM: Japanese encephalitis virus

<400> SEQUENCE: 61

Tyr Ser Ala Gln Val Gly Ala Ser Gln Ala Ala Lys Phe
1               5                   10

<210> SEQ ID NO 62
<211> LENGTH: 17
<212> TYPE: PRT
<213> ORGANISM: Japanese encephalitis virus

<400> SEQUENCE: 62

Asn His Gly Asn Tyr Ser Ala Gln Val Gly Ala Ser Gln Ala Ala Lys
1               5                   10                  15

Phe

<210> SEQ ID NO 63
<211> LENGTH: 19
<212> TYPE: PRT

```
<213> ORGANISM: Japanese encephalitis virus

<400> SEQUENCE: 63

Ser Glu Asn His Gly Asn Tyr Ser Ala Gln Val Gly Ala Ser Gln Ala
 1               5                  10                  15
Ala Lys Phe

<210> SEQ ID NO 64
<211> LENGTH: 11
<212> TYPE: PRT
<213> ORGANISM: Japanese encephalitis virus

<400> SEQUENCE: 64

Ile Lys Tyr Glu Val Ala Ile Phe Val His Gly
 1               5                  10

<210> SEQ ID NO 65
<211> LENGTH: 11
<212> TYPE: PRT
<213> ORGANISM: Japanese encephalitis virus

<400> SEQUENCE: 65

Gly Ala Leu His Gln Ala Leu Ala Gly Ala Ile
 1               5                  10

<210> SEQ ID NO 66
<211> LENGTH: 11
<212> TYPE: PRT
<213> ORGANISM: Japanese encephalitis virus

<400> SEQUENCE: 66

Gly Ile Phe Val His Gly Thr Thr Thr Ser Glu
 1               5                  10

<210> SEQ ID NO 67
<211> LENGTH: 10
<212> TYPE: PRT
<213> ORGANISM: Japanese encephalitis virus

<400> SEQUENCE: 67

His Val Leu Gly Arg Leu Thr Thr Val Asn
 1               5                  10

<210> SEQ ID NO 68
<211> LENGTH: 10
<212> TYPE: PRT
<213> ORGANISM: Japanese encephalitis virus

<400> SEQUENCE: 68

Glu Ala Trp Leu Asp Ser Thr Lys Ala Thr
 1               5                  10

<210> SEQ ID NO 69
<211> LENGTH: 8
<212> TYPE: PRT
<213> ORGANISM: Japanese encephalitis virus

<400> SEQUENCE: 69

Trp Val Arg Ala Ile Asp Val Gly
 1               5

<210> SEQ ID NO 70
<211> LENGTH: 14
<212> TYPE: PRT
```

```
<213> ORGANISM: Japanese encephalitis virus

<400> SEQUENCE: 70

Glu Thr Pro Arg Ser Leu Ala Lys Ile Val His Lys Ala His
1               5                   10

<210> SEQ ID NO 71
<211> LENGTH: 14
<212> TYPE: PRT
<213> ORGANISM: Japanese encephalitis virus

<400> SEQUENCE: 71

Ser Val Arg Thr Thr Thr Asp Ser Gly Lys Leu Ile Thr Asp
1               5                   10

<210> SEQ ID NO 72
<211> LENGTH: 12
<212> TYPE: PRT
<213> ORGANISM: Japanese encephalitis virus

<400> SEQUENCE: 72

Glu Asp Phe Gly Phe Gly Ile Thr Ser Thr Arg Val
1               5                   10

<210> SEQ ID NO 73
<211> LENGTH: 9
<212> TYPE: PRT
<213> ORGANISM: Japanese encephalitis virus

<400> SEQUENCE: 73

Thr Asp Leu Ala Arg Tyr Val Val Leu
1               5

<210> SEQ ID NO 74
<211> LENGTH: 12
<212> TYPE: PRT
<213> ORGANISM: Japanese encephalitis virus

<400> SEQUENCE: 74

Lys Ile Leu Pro Gln Ile Ile Lys Asp Ala Ile Gln
1               5                   10

<210> SEQ ID NO 75
<211> LENGTH: 13
<212> TYPE: PRT
<213> ORGANISM: Japanese encephalitis virus

<400> SEQUENCE: 75

Asp Thr Thr Thr Gly Val Tyr Arg Ile Met Ala Arg Gly
1               5                   10

<210> SEQ ID NO 76
<211> LENGTH: 9
<212> TYPE: PRT
<213> ORGANISM: Japanese encephalitis virus

<400> SEQUENCE: 76

Phe Leu Glu Leu Leu Arg Thr Ala Asp
1               5

<210> SEQ ID NO 77
<211> LENGTH: 15
<212> TYPE: PRT
<213> ORGANISM: Japanese encephalitis virus
```

```
-continued

<400> SEQUENCE: 77

Ser Ile Gly Gly Val Phe Asn Ser Ile Gly Lys Ala Val His Gln
1               5                   10                  15

<210> SEQ ID NO 78
<211> LENGTH: 10
<212> TYPE: PRT
<213> ORGANISM: Japanese encephalitis virus

<400> SEQUENCE: 78

His Val Leu Gly Arg Leu Thr Thr Val Asn
1               5                   10

<210> SEQ ID NO 79
<211> LENGTH: 10
<212> TYPE: PRT
<213> ORGANISM: Japanese encephalitis virus

<400> SEQUENCE: 79

Glu Ala Trp Leu Asp Ser Thr Lys Ala Thr
1               5                   10

<210> SEQ ID NO 80
<211> LENGTH: 14
<212> TYPE: PRT
<213> ORGANISM: Japanese encephalitis virus

<400> SEQUENCE: 80

Ser Val Arg Thr Thr Thr Asp Ser Gly Lys Leu Ile Thr Asp
1               5                   10

<210> SEQ ID NO 81
<211> LENGTH: 12
<212> TYPE: PRT
<213> ORGANISM: Japanese encephalitis virus

<400> SEQUENCE: 81

Glu Asp Phe Gly Phe Gly Ile Thr Ser Thr Arg Val
1               5                   10

<210> SEQ ID NO 82
<211> LENGTH: 9
<212> TYPE: PRT
<213> ORGANISM: Japanese encephalitis virus

<400> SEQUENCE: 82

Thr Asp Leu Ala Arg Tyr Val Val Leu
1               5

<210> SEQ ID NO 83
<211> LENGTH: 34
<212> TYPE: PRT
<213> ORGANISM: Japanese encephalitis virus

<400> SEQUENCE: 83

Ser Glu Asn His Gly Asn Tyr Ser Ala Gln Val Gly Ala Ser Gln Gly
1               5                   10                  15

Ser Ile Gly Gly Val Phe Asn Ser Ile Gly Lys Ala Val His Gln Val
            20                  25                  30

Phe Gly

<210> SEQ ID NO 84
<211> LENGTH: 19
```

```
<212> TYPE: PRT
<213> ORGANISM: Japanese encephalitis virus

<400> SEQUENCE: 84

Gly Ser Ile Gly Gly Val Phe Asn Ser Ile Gly Lys Ala Val His Gln
  1               5                  10                  15

Val Phe Gly

<210> SEQ ID NO 85
<211> LENGTH: 10
<212> TYPE: PRT
<213> ORGANISM: Japanese encephalitis virus

<400> SEQUENCE: 85

Pro Thr Leu Asp Val Arg Met Ile Asn Ile
  1               5                  10

<210> SEQ ID NO 86
<211> LENGTH: 13
<212> TYPE: PRT
<213> ORGANISM: Japanese encephalitis virus

<400> SEQUENCE: 86

Ala Ile Val Val Glu Tyr Ser Ser Ser Val Lys Leu Thr
  1               5                  10
```

CHIMERIC T HELPER-B CELL PEPTIDE VACCINE FOR JAPANESE ENCEPHALITIS VIRUS

FIELD OF INVENTION

This invention relates to chimeric T helper-B cell peptide as a vaccine for Japanese encephalitis virus.

BACKGROUND OF INVENTION

Amongst insect borne viral diseases, Japanese encephalitis and dengue have a notoriety of encompassing entire region of South East Asia. The envelope glycoprotein contains at least five determinants that seem to be correlated with the important biological properties of hemagglutination and neutralization. Envelope glycoprotein is responsible for the attachment of the virus and thus is associated with infectivity. The existing vaccine for Japanese encephalitis is purified, killed virus vaccine prepared from infant mouse brain that consists of mainly envelope glycoprotein of the virus. Three injections of mouse brain derived killed purified vaccine followed by a booster after 12 to 18 months, can give effective immunization as judged by induction of neutralizing antibodies. Mouse brain vaccine shows neutralizing antibodies against Indian strain also. The efficacy of the vaccine has been noted only if three doses are administered. U.S. Pat. No. 5,824,506 Chan, et al. Oct. 20, 1998 discloses Peptide antigens derived from the dengue virus type-2 glycoprotein NS1 are provided. The peptide antigens are specifically immunoreactive with sera from individuals infected with the dengue virus. The antigens are useful as diagnostic tools in determining whether an individual has been or is infected with dengue virus, and for discriminating between infection with dengue virus and infection with related flaviviruses. The antigens are also useful in vaccine compositions for immunizing individuals against infection with the dengue virus.

U.S. Pat. No. 5,494,671 Lai, et al. Discloses C-terminally truncated flavivirus envelope proteins 80-81% in size which are more immunogenic than their counterpart full-length proteins. The aforesaid patent further discloses recombinant viruses that encode the truncated protein and to host cells infected therewith. Host cells express the truncated protein on their outer membrane and secrete it into the medium. The patent discloses vaccines for use against flavivirus infection. The vaccines include either a recombinant vaccinia virus expressing the truncated envelope protein, and the truncated envelope protein produced by a recombinant baculovirus.

In China, attenuated Japanese encephalitis virus vaccine consisting of Japanese encephalitis virus strain SA 14-14-2 is being used. The attenuation has been carried out in hamster kidney cells and have unknown passage histories. Mice inoculated intracerebrally with the SA 14-14-2 vaccine strains survived without showing any signs of CNS involvement. The virus titers in brains persisted at low levels for several days and could not be detected after 10 days (Hase T, Dubois, Dr. Summers, P L, Downs, M B and Ussery, M A. (1993) Comparison of replication rates and pathogenicities between the SA14 parent and SA 14-14-2 vaccine strains of Japanese encephalitis virus in mouse brain neurons. Arch Virol 130 131-43. Dubois T., Dr. Summers, P L. Downs, M B and Ussery, M A (1993) Comparison of replication rates and pathogenicities between the SA14 parent and SA 14-14-2 vaccine strains of Japanese encephalitis virus in mouse brain neurons. Arch Virol 130 131-43). The safety and immunogenicity of this vaccine has been tested. 1,026 children between the ages of 5 and 12 years, were vaccinated with live-attenuated Japanese encephalitis virus vaccine. None of the group of 47 of the vaccinated children, has temperature >37.4° C. Seroconversion rates in seronegative children were 100% (GMT 35.3) (Xin Y Y, Ming, Z G, Peng, G Y, Jain, A and Min, L H (1988) Safety of a live-attenuated Japanese encephalitis virus vaccine (SA14-14-2) for children. Am J Trop Med Hyg 39 214-7). Many attempts are being carried out to develop recombinant vaccine for Japanese encephalitis virus. These include expression of various proteins and then immunizing animals with the products. It was realized very early that expression and immunization with envelope glycoprotein alone was not very useful (Mason P W, McAda, P C, Dalrynple, J M, Fournier, M J and Mason, T L (1987) Expression of Japanese encephalitis virus antigens in *Escherichia coli*. Virology 158 361-72). Mice immunized with recombinant baculovirus infected cells containing envelope glycoprotein and NS-1 genes were challenged with Japanese encephalitis virus. Survival was increased from about 30% in unimmunized mice to 70% in envelope glycoprotein and polyprotein recipients but not in NS-1 recipients (McCown J, Cochran, M, Putnak, R, Feighny, R, Burrous, J, Henchal, E and Hoke, C (1990). Protection of mice against lethal Japanese encephalitis with a recombinant baculovirus vaccine. Am J Trop Med Hyg 42 491-9). Immunization of mice with purified extracellular subviral particles composed of prM and E proteins in recombinant vaccinia viruses could protect mice from 4.9× $10^5$ LD50 of Japanese encephalitis virus. (Konishi E, Pincus, S, Paoletti, E, Shope, R E, Burrage, T and Mason, P W. (1992) Mice immunized with a subviral particle containing the Japanese encephalitis virus prM/M and E proteins are protected from lethal JEV infection. Virology 188 714-20). These particulate antigens were also shown to induce Japanese encephalitis virus specific CTL response in mice. (Konishi E, Win, K S, Kurane, I, Mason, P M, Shope, R E and Ennis, F A (1997) Particulate vaccine candidate for Japanese encephalitis induces long-lasting virus-specific memory T lymphocytes in mice. Vaccine 15 281-6).

Vaccinia recombinants that co-expressed the genes for pre-membrane and envelope glycoprotein elicited high levels of neutralizing and HI antibodies in mice and protected mice from a lethal challenge by Japanese encephalitis virus. Recombinants expressing only the gene for NS1 induced antibodies to NS1 but provided low levels of protection from a similar challenge dose of Japanese encephalitis virus. Immunization of mice with vaccinia recombinant viruses containing PrM gene along with NS-1 and envelope glycoprotein protected them from challenge with Japanese encephalitis virus. Pox virus (Canary pox and vaccinia) based Japanese encephalitis recombinant vaccines have been constructed and shown to produce Japanese encephalitis virus specific CTLs in mice. (Konishi, E, Kurane, I Mason, P W, Shope, R E and Ennis, F A (1997) Poxvirus-based Japanese encephalitis vaccine candidates induce J E virus specific CD8+ cytotoxic T lymphocytes in mice. Virology 227 353). Poxvirus-based recombinant J E vaccine candidates, NYVAC-JEV and ALVAC-JEV, encoding the Japanese encephalitis virus prM, E and NS1 proteins were examined for their ability to induce Japanese encephalitis virus-specific CTLs. The volunteers received subcutaneous inoculations with each of these candidates on days 0 and 28. Anti-E and anti-NS1 antibodies were elicited in a most vaccinees inoculated with NYVAC-JE virus and in some vaccinees inoculated with ALVAC-JEV, PBMCs obtained from approximately one half of vaccinees showed positive proliferation in response to stimulation with live Japanese encephalitis virus. Presence of the Japanese encephalitis virus-specific CDS+CD4- cytotoxic T cells in vitro-stimulated peripheral blood mononuclear cells obtained from two NYVAC-JEV and two ALVAC-JEV vaccinees was demonstrated. (Konishi E, Kurane, I, Mason, P M, Shope, R E, Kanesa-Thasan, N, Smucny, J J, Hoke, C H Jr and Ennis, F A (1998). Induction of Japanese encephalitis virus-specific cytotoxic T lymphocytes in humans by poxvirus-based J E vaccine candidates. Vaccine 16 842-9). A chimeric Yellow fever (YF)/JE virus (ChimeriVax-JE virus) was constructed by insertion of the prM and envelope glycoprotein genes of an attenuated human vaccine strain (SA14-14-2) of Japanese encephalitis virus between C and NS genes of a YF 17D infectious clone. Mice inoculated subcutaneously with one dose of $>/=10^3$ pfu of ChimeriVax-JE virus were protected against IP challenge with a virulent Japanese encephalitis virus.

In recent years, it has been shown that fragments of proteins in the form of synthetic peptides can be used to induce T helper and antibody responses. Attempts to delineate B cell epitopes from Japanese encephalitis virus have resulted in delineation of Met 303 to Trp 396 as the shortest sequence capable of reacting with 10 MAbs. Disulfide bond between cys 304 and 335 was required for presentation of the binding site(s) for these MAbs. However, it was not an effective immunogen for inducing neutralizing or protective antibodies in mice (Mason P W, Dalrymple, J M, Gentry, M K, McCown, J M, Hoke, C H, Burke, D S, Fournier, M J and Mason, T L (1989) Molecular characterization of a neutralizing domain of the Japanese encephalitis virus structural glycoprotein. J Gen Virol 70 2037-49). The fragment carrying the coding sequence of amino acid 373-399 of envelope glycoprotein elicited the highest neutralizing antibody titer (1:75). HI antibodies were not induced by this fusion protein (Seif S A, Korita, K and Igarashi, A (1996) A 27 amino acid coding region of E virus protein expressed in *E. coli* as fusion protein with glutathione-S-transferase elicit neutralizing antibody in mice. Virus Res 43 91-6). Neutralizing antibody inducing epitopes have been detected on C terminal regions of envelope glycoprotein (Seif S A, Morita, K, Matsuo, S, Hasebe, F and Igarashi, A (1995) Finer mapping of neutralizing epitope(s) on the C-terminal of Japanese encephalitis virus E-protein expressed in recombinant *Escherichia coli* system. Vaccine 13 1515-21 and Jan L R, Yang, C S, Henchal, L S, Sumiyoshi, H, Summers, P L, Dubois D R and Lai, C J (1993) Increased immunogenicity and protective efficacy in outbred and inbred mice by strategic carboxyl-terminal truncation of Japanese encephalitis virus envelope glycoprotein. Am J Trop Med Hyg 48 412-23) Peptides from C protein have also been delineated for reactivity with sera from Japanese encephalitis and dengue patients. Pep91-105 and 8-22 belonged to group-specific epitopes that reacted with both Japanese encephalitis and dengue-1 patient sera. Pep 1-15 and 34-48 belonged to subcomplex-specific epitopes that reacted only with Japanese encephalitis but not with dengue-1 patient sera. (Huang J H, Wey, J J, Lee, H F, Tsou) T L, Wu, C S, Wu, J R, Chen, H M, Chin, C, Chien, L J, Chen, L K, Wu Y C, Pan, M J and Wang, T M (1996) Identification of immunodominant, group-specific and subcomplex-specific, continuous epitopes in the core regions of Japanese encephalitis virus using synthetic peptides. Virus Res 41 43-53).

DISADVANTAGES OF THE PRIOR ART

In case of mouse brain derived killed purified vaccine, three doses of the injectable vaccine are to be administered. In a trial with vaccine made in Japan was carried out in South Arcot district of Tamil Nadu, India. Of a total of 113 school children, 72% showed antibody response while the responders increased to 87.8% after booster dose of Biken Japanese encephalitis vaccine after one year. Only about 20 per cent of the children had persisting antibodies one year after the primary vaccination. (Mohan Rao C V R, Risbud, A R, Dandawate, C N, Umarani, U B, Ayachit, V M, Rodrigues, F M and Pavri, K M (1993) Serological response to Japanese encephalitis vaccine in a group of school children in South Arcot district of Tamil Nadu Indian J Med Res 97 53-59). The problems of strain variation and the protection offered by the inactivated vaccine based on Nakayama have always been noted.

In case of attenuated Japanese encephalitis vaccine used in China, although efficacy of the vaccine has been proven in many studies by now, there are some problems associated with the licensing of this vaccine all over the world. The passage history and the laboratory practices, which were used in generation of this vaccine, have not been known completely. Thus, attempts to re-invent the attenuated strain from the same SA14-14-2 strain have been carried out. In a Japanese study antibodies against both envelope glycoprotein and NS 1 were observed in mice infected with the attenuated Japanese encephalitis virus strain SA(A) derived from the live Japanese encephalitis vaccine strain SA14-14-2. (Lee T, Komiya, T, Watanabe, K, Aizawa, C and Hashimoto, H (1995) Immune response in mice infected with the attenuated Japanese encephalitis vaccine strain SA14-14-2. Acta Virol 39 161-4).

The problems associated with vaccine for Japanese encephalitis are, e.g. discrepancy in the age at which Japanese encephalitis vaccine should be administered. The cost of currently available vaccine is very high. The additional cost of administering three doses will also have to be taken into consideration. It is not known whether the effect of Japanese encephalitis vaccine will be long lasting, in absence of exposure to Japanese encephalitis after the third dose. Whether yearly boosters are required or not, until natural immunity due to natural Japanese encephalitis infection is not known. Thirdly, immune response to Japanese encephalitis virus is very low (Pavri K M (1984)) Problems of JE immunization in India. Proc. Of National Conference on Japanese encephalitis. Ind.J. Med. Res Suppl pp 81-84) In addition, the question of immunity to the local strains by Nakayama or Beijing strains of virus used in vaccine will have to be taken into consideration. As the vaccine is mouse brain derived there are allergic reactions to the vaccine and the frequencies of allergic mucocutaneous reactions varied from 1-17 per 10,000 vaccinees during 1983-1995 (Plesner A M and Ronne, T (1997) Allergic mucocutaneous reactions to Japanese encephalitis vaccine. Vaccine 15 1239-43).

13. How these drawbacks have been overcome by your invention. In recent years, it has been shown that fragments of proteins in the form of synthetic peptides can be used to induce T helper and antibody responses. (Ref) Thus, neutralizing antibody-inducing epitopes from envelope glycoprotein have been delineated. As these peptide sequences are not sufficient for inducing protective immunity, a chimeric peptide has been prepared incorporating T helper epitope along with the virus neutralizing antibody inducing B cell epitope. This will ensure that both T helper and B cell immunity is generated for the protection from Japanese encephalitis virus challenge. The said chimeric vaccine is designed and thus more than one chimeric peptide can be added to formulate the effective vaccine as per requirement in the future.

OBJECTS OF THE INVENTION

Figure 1:
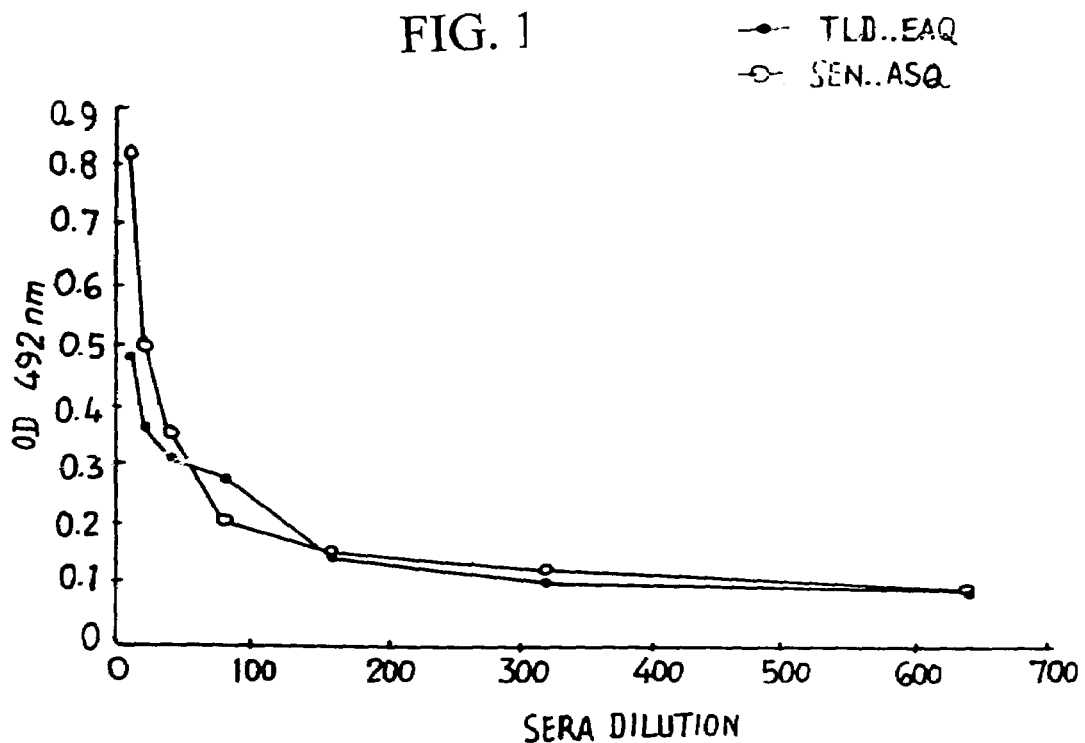
FIG. 1 shows ELISA assays to test anti Japanese encephalitis virus immune responses, at varying dilutions of sera. The peptide labeled "TSD . . . EAQ" is SEQ ID NO:56; the peptide labeled "SEN . . . ASQ" is SEQ ID NO:57.

It is an object of the present invention to propose safe and effective vaccines against flaviviruses for humans and animals. Various other objects and advantages of the present will become apparent from the ensuing description.

DESCRIPTION OF THE INVENTION

According to this invention there is provided a vaccine composition for humans and animals against Japanese encephalitis virus infection, comprising a chimeric synthetic peptide, said chimeric peptide selected from envelope glycoprotein, consisting of: amino acids Egp 149-SENH-GNYSAQVGASQ-163 (SEQ ID NO:1) and Egp 428-GSIG-GVFNSIGKAVHQVFG-446 (SEQ ID NO:84) of Japanese encephalitis virus glycoprotein wherein chimeric peptide is in an amount sufficient to induce protective immunity against Japanese encephalitis virus infection.

In one embodiment, the present invention relates to vaccine composition for humans and animals against or Japanese encephalitis virus infection, comprising a chimeric synthetic peptide. Chimeric peptide was selected from envelope protein, consists of amino acids 149-SENHGNYSAQV-GASQAAKF-167 (SEQ ID NO: 3) AND 427-GSIGGVFN-SIGKAVHQVFG-445 (SEQ ID NO: 84).

In another embodiment, the present invention also relates to the vaccine composition wherein said peptide 149-SENH-GHNYSAQVAGASQAAKF-167 (SEQ ID NO: 3) induces neutralizing antibodies against Japanese encephalitis virus.

In another embodiment, the present invention also relates to the vaccine composition wherein said peptide 149-SENH-GHYSAQVGASQAAKF-167 induces neutralizing antibodies against Japanese encephalitis virus.

In a further embodiment, it also relates to a vaccine composition for humans and animals against Japanese Encephalitis Virus infection comprising a neutralizing antibody inducing peptide sequences from envelope glycoprotein of Japanese encephalitis virus. The said sequences are amino acids 39-PTLDVRMINIEA -50 (SEQ ID NO:4), 273-EYSSSVKLTSG-283 (SEQ ID NO:5).

In another embodiment, the present invention also relates to peptide sequences from Japanese encephalitis virus envelope glycoprotein, Capsid protein, Membrane protein, Non Structural protein-1 and Non Structural protein-3 capable of stimulating T helper cells from immunized animals.

In another embodiment, the present invention also relates to a combination of peptides mentioned above resulting in chimeric T helper B cell peptides capable of inducing protective immunity against Japanese encephalitis virus infection.

Either B or T lymphocytes through their receptors may define epitopes as the regions of part of proteins that are recognized. Based can the cell involved epitopes may be classified as B cell, T helper cell or CTL epitopes that stimulate B cells, T helper (CD4+) and CTLs respectively. MHC molecules present T cell epitopes to the TCR present on the T cells. B cell epitopes in contrast to the T cell epitopes have dependence on the three dimensional structure. B cell epitopes can be predicted using several different methods B cell determinants of envelope glycoprotein of Bakura (India) strain (733913) were identified. Briefly, antigenic propensity values are assigned to each of the twenty amino acid residues based an their frequency of occurrence in experimentally confirmed B cell antigenic determinants. These parameters along with appropriate cutoff values were used in a computer program developed. Table 1 shows the predicted B cell determinants of envelope glycoprotein of Japanese encephalitis virus.

TABLE 1

Predicted B cell epitopes from envelope glycoprotein of Japanese encephalitis virus.

(SEQ ID NOS 6-29, respectively in order of appearance)

TABLE 1

| Predicted B cell epitopes from envelope glycoprotein of Japanese encephalitis virus. (SEQ ID NOS 6-29, respectively in order of appearance) | |
| --- | --- |
| Kolaskar & Tongaokar's method | Kutubuddin et al 1993 |
| 18-TWVDLVLE6DSCLTIM-33 | |
| 40-TLDVRMI-46 | |
| 48-IEAVQLAEVRSYCYHASVTDISTVARCP-75 | 75-CPTTGEAHNEKRADSSYV-92 |
| 88-SSYVCKQG-95 | |
| 113-IDTCAKFSCTSK-124 | |
| 155-YSAQVGASQAAKFTVTPNAPSITLKL-180 | 147-TTTSENHGNYS-157 |
| 155-YSAQVGASQAAKFTVTPNAPSITLKLGD-182 | |
| 185-EVTLDCE-191 | |
| 199-EAFYVMTV-206 | |
| 208-SKSFLVHRE-216 | 226-WTPPSSTAWRNR-237 |
| 262-LHQALAG-268 | 243-FEEAHATKQ-251 |
| 273-EYSSSVKLTSGHLKCRLK-290 | |

TABLE 1-continued

Predicted B cell epitopes from envelope
glycoprotein of Japanese encephalitis virus.
(SEQ ID NOS 6-29, respectively in order
of appearance)

| Kolaskar & Tongaokar's method | Kutubuddin et al 1993 |
|---|---|
| 292-DKLALKG-298 | 309-FAFAKNPADTG-319 |
| 320-GTVVIELSYS-329 | 328-SYSGSDGP-335 |
| 351-VGRLVTVN-358 | |
| 367-NSKVLVEME-375 | 363-ATSSANS-369 |
| 379-GDSYIVVGR-387 | |

The Table 1 depicts amino acid sequences predicted from envelope glycoprotein of Japanese encephalitis virus Amino acid sequence derived is from Japanese encephalitis virus strain Bankura (733913).

In order to arrive at the unique sequences that might be useful in vaccine development amino acid sequences from other related flaviviruses viz., WHV, MVEV, DENV and YFV were downloaded from protein data banks and multiple alignments were carried out using CLUSTAL program. Similarly in order to understand amino acid sequences from a few Japanese encephalitis virus strains were also subjected to multiple alignment.

The multiple alignments were carried cut CLUSTAL program.

The region in the envelope glycoprotein which were identified as being non-homologous with other flaviviruses were:
1. 149-SENHGNYSAQVGASQ-163 (SEQ ID NO. 1)
2. 40-TLDVRMINIEA50 (SEQ ID NO. 30)
3. 270-IVVEYSSSVKLTS-282 (SEQ ID NO. 31)

Figure 2:
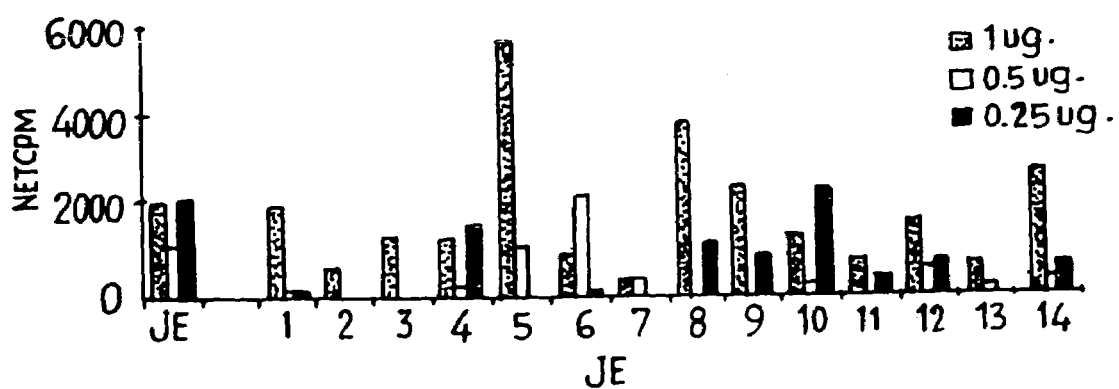
FIG. 2 shows T helper cell proliferation assays, which demonstrate the stimulation of Japanese encephalitis virus immune splenocytes with T helper peptides.

These sequences were conserved within different Japanese encephalitis virus strains (as shown in FIG. 2 of U.S. published patent application, 20040076634). This means that regions 40-50, 155-163 and 270-290 are unique to Japanese encephalitis virus. Antibodies induced against these peptides from envelope glycoprotein would thus have better chances of being neutralizing antibody. It should be noted here that there are no major differences between the amino acid sequence of Japanese encephalitis virus Nakayama strain and Bankura strain.

SYNTHESIS OF PEPTIDES

These peptides were synthesized by time standard solid phase synthesis protocols. The synthesis was carried out using FMOC(9-Fluorenylmethoxycarbonyl) amino acid pentafluoraphenyl (O PFP) esters on Novasyn PA 500 resin (Novabiochem Ltd. UK) that yielded peptide acids on cleavage. Completion of the coupling of amino acid was strictly monitored to avoid short substituted peptides by qualitative monitoring of the coupling reaction color test for detection of free terminal amino groups in the solid-phase for detection of free amino groups. Coupling also was checked at 290 na by monitoring the FMOC group released during the deprotection step by 20% piperidine solution in dimethyl formamide. Peptides were cleaved from the resin by trifluoroacetic acid (TFA) with appropriate scavengers dictated by the sequence. The peptides were precipitated in super dry diethyl ether. The ether precipitated peptides were purified an HPLC and peaks collected. The purity was checked by assessing the single peak elution of the peptide under a linear gradient elution of 80% acetonitrile in water containing 0.1% TFA on reverse phase 18 column. Purified peptides were lyophilized and stored at −20.

Any peptide with a purity >85% was used fair conjugation purposes. Alternatively, peptide in the region of 270-290 were synthesized on Pin head peptide synthesis modules using Fmoc amino acids using manufacturer's protocols. Side chains of these peptides were also cleaved by Trifluoroacetic acid cleavage keeping peptides attached to the pins.

Reactivity of Peptides with Monoclonal Antibodies against JE Virus

A panel of anti Japanese encephalitis virus monoclonal antibodies that have different immunological properties Epitope mapping of Japanese encephalitis virus envelope protein using monoclonal antibodies against an Indian strain have been developed at NIV. These MAbs were used to probe the antigenicity of the peptides. The purpose of this study was to determine the epitope recognized by the MAbs and also find the optimum peptide length and sequence as an epitope. This, would also elucidate the structural requirement if any, for antibody binding. The MAbs included Hs-1, Hs-2, Hs-3 that are Japanese encephalitis virus specific, Hemagglutination inhibition (HI) positive Epitope mapping of Japanese encephalitis virus envelope protein using monoclonal antibodies against an Indian strain. J Gen Virol 69 2741-7). Peptides (1 μg/well) were passively coated on ELISA wells (Immulon II, Nunc) using $Na_2CO_3/HCO_3$ buffer pH 9.6. Blocking was carried out by 1% BSA in PBS. Reaction of with peptide and washing were carried out in 1% BSA in PBS (0.01 M phosphate 0.15 M NaCl, pH 7.2). Monoclonal antibody was diluted either 1:50 or 1:100 for reaction. Hundred micro liters of antibody diluted in 1% BSA in PBS, was added and incubated for 60 min at 37° C. After washing with PBS containing 0.1% Tween 20, bound antibodies (Sigma, USA). In case of ELISA on Pin heads after blocking pins with peptides were dipped into wells containing antibody. The color development was carried out using $H_2O_2$ and O-phenyl diamine (OPD) as the chromogen. The OD values were monitored at 492 nm. Epitope mapping of Japanese encephalitis virus envelope protein using monoclonal antibodies against an Indian strain. SP2/0 AF was used as negative control. "Data in Table 2 clearly indicates that peptides 39-PTLD-VRMI-46 (SEQ ID NO: 38) and 269-AIVVEYSS-276 (SEQ ID NO: 48) react with MAb Hs-1 and peptide 151-NH-GNYSAQVGASQAAKF-167 (SEQ ID NO: 34) reacts with MAb Hs-2 and MAb Hs-3.".

ELISA with JE Virus

ELISA wells (Nunc Immulon II) were coated with purified JE antigen (10 g/well) overnight, in sodium carbonate buffer (0.05 M, pH 9.8). Subsequently, wells were blocked with 1% bovine serum albumin (BSA) in PBS (0.01 M phosphate 0.15

M NaCl, pH 7.2). Hundred micro liters of antibody diluted in 1% ovalbumin in PBS, was added and incubated for 60 min at 37° C. After washing with PBS containing 0.1% Tween 20, bound antibody was probed with goat-anti mouse 1 g-horseradish peroxidase conjugated antibodies (Sigma, USA). The color development was carried out using $H_2O_2$ and O-phenyl diamine (OPD) as the chromogen. The OD values were monitored at 492 nm (Cecilia et. al., 1988). Antibody response against JE virus was tested for anti-peptide antibody sera. In all these experiments, sera from PBS control mice and ovalbumin immunized mice were used as negative controls. Polyclonal immune AF was used as the positive control and peritoneal AF from the nonimmune mice was used as negative control. In experiments with MAbs, AF obtained from SP2/0 inoculated mice were used as negative control.

TABLE 2

Reactivity of Peptides with monoclonal Antibodies against JE virus (SEQ ID NOS 35-46,1,47,34,3,48-55, respectively in order of appearance)

TABLE 2

Reactivity of Peptides with monoclonal Antibodies against JE virus
(SEQ ID NOS 35-46, 1, 47, 34, 3, 48-55, respectively in order of appearance)

| PEPTIDE | Hs-1 | Hs-2 | Hs-3 |
|---|---|---|---|
| 33-IMANDKPT-40 | 0.110 | 0.016 | 0.017 |
| 35-ANDKPTLD-42 | 0.022 | 0.016 | 0.052 |
| 37-DKPTLDVR-44 | 0.029 | 0.016 | 0.035 |
| 39-PTLDVRMI-46 | 0.313 | 0.006 | 0.025 |
| 40-TLDVRMIN-47 | 0.329 | 0.008 | 0.064 |
| 41-LDVRMINI-48 | 0.277 | 0.007 | 0.082 |
| 42-DVRMINIE-49 | 0.155 | 0.008 | 0.043 |
| 43-VRMINIEA-50 | 0.338 | 0.012 | 0.133 |
| 45-MINIEASQ-52 | 0.177 | 0.001 | 0.080 |
| 47-NIEASQLA-54 | 0.07 | 0.003 | 0.081 |
| 155-YSAQVGASQ-163 | 0.118 | 0.492 | 0.334 |
| 151-NHGNYSAQVGASQ-163 | 0.074 | 0.294 | 0.258 |
| 149-SENHGNYSAQVGASQ-163 | 0.093 | 0.415 | 0.377 |
| 155-YSAQVGASQAAKF-167 | 0.106 | 0.501 | 0.377 |
| 151-NHGNYSAQVGASQAAKF-167 | 0.084 | 0.561 | 0.259 |
| 149-SENHGNYSAQVGASQAAKF-167 | 0.095 | 0.412 | 0.400 |
| 269-AIVVEYSS-276 | 0.696 | 0.041 | 0.115 |
| 270-IVVEYSSS-277 | 0.637 | 0.030 | 0.112 |
| 271-VVEYSSSV-278 | 0.659 | 0.029 | 0.090 |
| 272-VEYSSSVK-279 | 0.290 | 0.040 | 0.106 |
| 273-EYSSSVKL-280 | 0.538 | 0.045 | 0.110 |
| 274-YSSSVKLT-281 | 0.616 | 0.054 | 0.153 |
| 275-SSSVKLTS-276 | 0.765 | 0.053 | 0.136 |
| 276-SSVKLTSG-277 | 0.447 | 0.061 | 0.123 |

Conjugation of peptide with carrier immunization of mice Peptides 40-TLDVRMINIEASQ-52 (SEQ ID NO: 56) AND 149-SENHGNYSAQVGASQA-164 (SEQ ID NO: 57) were synthesized, purified, and conjugated to the carrier molecule. The carrier molecule used in these experiments was Ovalbumin (OA). The peptide was dissolved in HEPES buffer (50 mM pH 8.5) at a concentration of 10 mg ml$^{-1}$ was kept for stirring. While stirring, equal volume of Citraconic anhydride solution (in water 10 mg ml$^{-1}$) was slowly added. During the reaction pH was maintained between 8-9. The reaction mixture was incubated for one hour at room temperature. The peptide was diluted to a concentration of 1 mg ml$^{-1}$. EDC (3-dimethyl-aminopropyl-3-ethyl carbodiimide) was added to it at a final concentration of 10 mg ml$^{-1}$, the pH was kept at 8.0. After a incubation at room temperature for 5 min, equal volume of Ovalbumin was added at a molar ratio of 1:20 (Carrier:Peptide). The reaction was incubated at room temperature for four hrs and was terminated by Sodium acetate pH 4.2 to a final concentration of 100 mM. After incubation for one hour, solution was dialyzed against Sodium acetate pH 4.2 and then against 12 liters of PBS with four changes over 12 hours. The peptide protein conjugate was lyophilized and stored below 0° C.

For immunization, 40 μg of peptide-protein conjugate emulsified in Freund's complete adjuvant (1:1) was injected by sub cutaneous route in mice. A group of four mice was used per peptide-protein carrier conjugate. Two boosters containing the similar amount of peptide-carrier conjugate were administered at weekly intervals in Freund's incomplete adjuvant. Control groups received carrier protein without peptide and PBS, emulsified with adjuvant. The mice were bled from the retro-orbital plexus, on 7th, 14th and 21st days post immunization for checking the antibody titer. Sera were separated and stored at –20.degree° C. until used. Anti Japanese encephalitis virus immune response was checked by ELISA where the anti-peptide sera was allowed to react with the native Japanese encephalitis virus virion by the method mentioned above. FIG. 1 shows the reactivity at different dilutions. In ELISA In order to fine tune this region in terms of antibody eliciting and antibody binding capacity, set of overlapping peptides were synthesized that were used to probe the same. Following overlapping peptides were synthesized

| | |
|---|---|
| 155-163 (SEQ ID NO: 45) | YSAQVGASQ |
| 151-163 (SEQ ID NO: 46) | NHGNYSAQVGASQ |
| 149-163 (SEQ ID NO: 1) | SENHGNYSAQVGASQ |
| 155-167 (SEQ ID NO: 47) | YSAQVGASQAAKF |
| 151-167 (SEQ ID NO: 34) | NHGNYSAQVGASQAAKF |

All these peptides were conjugated to ovalbumin as essential According to protocol mentioned above. Four BALB/c mice each were immunized with 40 ug per mouse per dose of these peptide OA conjugates along with Freund's adjuvant. The mice were administered booster doses at weekly intervals and bled through the retro-orbital route at weekly intervals. The anti Japanese encephalitis virus response was monitored by ELISA by the method mentioned above. Values mentioned are mean optical density readings obtained.

TABLE 3

Reactivity of Anti peptide sera with Japanese encephalitis virus By ELISA

TABLE 3

Reactivity of Anti peptide sera with Japanese encephalitis virus by ELISA

| Mice immunized with adjuvant + | Sera collected on post inoculation days | | |
|---|---|---|---|
| conjugated with peptide | 7 | 14 | 21 |
| 155YSAQVGASQ163 | 0.212 + | 0.236 + | 0.195 + |
| (SEQ ID NO: 58) | 0.076 | 0.028 | 0.047 |
| 151NHGNYSAQVGASQ163 | 0.286 + | 0.270 + | 0.246 + |
| (SEQ ID NO: 59) | 0.153 | 0.62 | 0.090 |
| 149SENHGNYSAQVGASQ163 | 0.242 + | 0.268 + | 0.268 + |
| (SEQ ID NO: 60) | 0.157 | 0.096 | 0.057 |
| 155YSAQVGASQAAKF167 | 0.223 + | 0.262 + | 0.198 + |
| (SEQ ID NO: 61) | 0.037 | 0.067 | 0.0178 |

TABLE 3-continued Reactivity of Anti peptide sera with Japanese encephalitis virus by ELISA

| Mice immunized with adjuvant + conjugated with peptide | Sera collected on post inoculation days | | |
|---|---|---|---|
| | 7 | 14 | 21 |
| 151NHGNYSAQVGASQAAKF167 (SEQ ID NO: 62) | 0.226 + 0.060 | 0.220 + 0.033 | 0.144 + 0.021 |
| 149SENHGNYSAQVGASQAAKF167 (SEQ ID NO: 63) | 0.191 + 0.058 | 0.255 + 0.050 | 0.217 + 0.029 |
| Ovalbumin | 0.127 + 0.022 | 0.116 + 0.072 | 0.153 + 0.003 |
| PBS | 0.113 + 0.034 | 0.124 + 0.029 | 0.183 + 0.029 |

The Table 3 shows the reactivity of the antipeptide antibodies against Japanese encephalitis virus by ELISA. Anti peptide antibody response reactive to Japanese encephalitis virus could be observed in all peptide immunized mice by 7th day. P1, i.e after the first dose. Antisera against all peptides showed reactivity with native Japanese encephalitis virus in ELISA confirming the correctness of the prediction method.

Delineation of T Helper Epitopes from Structural and Non-structural Proteins of Japanese Encephalitis Virus The importance of T helper cells in the immune response is well known. In course of development of B cells and maturation of immune response. B cells require certain localized cognate signals and cell-cell contact originating from T cells. Using combination of methods to predict amphipathic, tetramer and pentamer motifs, along with prediction of helix preferers and sequences which would have I-A and I-E binding motifs were predicted for all proteins of JE virus. Prediction of Th epitopes was carried out using EPIPLOT which included, amphipathic helix segments predicted by AMPHI program developed by Margalit et al (Margalit H, Sponge J. L., Cornette J. L., Cease K. B, DeLisi C. and Berzofsky J. A. (1987) Prediction of immunodominant helper T cell antigenic sites from the primary sequence. J. Immunology 138, 2213-2229). For prediction of amphipathic segments Fauchere and Pliska hydrophobicity scales of amino acids were used, block length of seven was selected. Fauchere J. L. and Pliska V., (1983) Hydrophobic parameters II of amino acid side chains from the partitioning of N-acetyl amino acid Eur. J. Med. Chem. 18, 369-375. Tetramer and pentamer motif [charged residues or glycine followed by 2-3 hydrophobic residues and then a polar residue] by Rothbard and Taylor (Rothbard J. and Taylor W. R. (1988) A common sequence pattern in T cell epitopes. EMBO J.7, 93-100). Prediction of sequence motifs of immunodominant secondary structures capable of binding to MHC [Ia/Ie] with high affinity was carried out by method of [Sette et al]. (Sette A., Buus S., colon S., Miles C. and Grey H. M. (1989) Structural analysis of peptides capable of binding to more than one Ia antigen. J. Immunol 142, 35-40). Multiple alignment of flaviviruses by using ALIGN program to choose flavivirus cross-reactive Th epitopes. T helper peptides with high scores in each of these prediction programs were chosen. Cross-reactive epitopes were chosen on the basis of homology amongst flaviviruses. After sequence alignments and homology analysis between various flaviviruses 14 peptide sequences were chosen.

These peptides were synthesized on Chiron Pin-head modules using cleavable option as per the manufacturer's methodology. Peptides were cleaved by Trifluroacetic acid method as mentioned above. BALB/c mice were primed with 0.1 ml,$10^{-2}$ dilution of mouse brain live Japanese encephalitis virus, West Nile virus intra-peritonealy, Primed mice were inoculated sub-cutaneously with 0.1 ml of Japanese encephalitis virus, West Nile virus inactivated mouse brain antigen [10 ug] and Normal antigen in equal volume of Complete Freund's adjuvant. Booster dose of above antigens were given similarly in Incomplete Freund's Adjuvant four days before harvesting. T helper cell proliferation assay was performed using spleenocytes from immunized and unimmunized mice. Spleenocytes were added to 96-well flat bottom plates at a concentration of 2*$10^5$ cells/well/0.1 ml. Cultures were stimulated with 0.1 ml of JEV antigen [5,2.5 & 1 ug/ml] and peptide [10,5 & 2.5 ug/ml] After 6 days, cultures were pulsed with 1 uCi [$^3$H] Thymidine for 18 h. Cells were harvested and counted for radioactivity. Values are depicted as Net cpm Net cpm=cpm in virus immune lymphocytes-cpm in non-immune lymphocytes. As shown in the Figure and Table peptides especially from the nonstructural proteins of JE virus have shown better stimulation.

FIG. 2 shows the stimulations of Japanese encephalitis virus immune spleenocytes with T helper peptides.

TABLE 4 delineation of T helper peptides from JE virus

TABLE 4 delineation of T helper peptides from JE virus

| | Protein | Sequence | Response to | |
|---|---|---|---|---|
| | | | JE | WN |
| Peptide 1 | WN Egp (SEQ ID NO: 64) | 135-IKYEVAIFVHG-145 | ++ | + |
| Peptide 2 | JE Egp (SEQ ID NO: 65) | 260-GALHQALAGAI-270 | − | − |
| Peptide 3 | JE Egp (SEQ ID NO: 66) | 140-GIFVHGTTTSE-150 | + | + |
| Peptide 4 | JE Egp (SEQ ID NO: 67) | 346-HVLGRLTTVN-355 | +++ | − |
| Peptide 5 | JE M (SEQ ID NO: 68) | 17-EAWLDSTKAT-26 | ++++ | − |
| Peptide 6 | JE PrM (SEQ ID NO: 69) | 36-WVRAIDVG-43 | ++ | − |
| Peptide 7 | JE NS1 (SEQ ID NO: 70) | 37-ETPRSLAKIVHKAH-50 | + | − |
| Peptide 8 | JE NS1 (SEQ ID NO: 71) | 297-SVRTTTDSGKLITD-310 | ++++ | + |
| Peptide 9 | JE NS1 (SEQ ID NO: 72) | 156-EDFGFGITSTRV-167 | ++++ | − |
| Peptide 10 | JE NS1 (SEQ ID NO: 73) | 404-TDLARYVVL-412 | +++ | ++ |
| Peptide 11 | JE NS3 (SEQ ID NO: 74) | 202-KILPQIIKDAIQ-212 | + | − |
| Peptide 12 | JE NS3 (SEQ ID NO: 75) | 17-DTTTGVYRIMARG-29 | ++ | ++ |
| Peptide 13 | JE NS3 (SEQ ID NO: 76) | 534-FLELLRTAD-543 | + | − |
| Peptide 14 | JE Egp (SEQ ID NO: 77) | 439-SIGGVFNSIGKAVHQ-455 | +++ | + |

Based On the results shown in FIG. and Table following peptides have been chosen as candidate T helper cell peptides to be incorporated in Chimeric T helper B cell vaccine.

| JE Egp | 346-HVLGRLTTVN-355 (SEQ ID NO: 78) |
| --- | --- |
| JE M | 17-EAWLDSTKAT-26 (SEQ ID NO: 79) |
| JE NS1 | 297-SVRTTTDSGKLITD-310 (SEQ ID NO: 80) |
| JE NS1 | 156-EDFGFGITSTRV-167 (SEQ ID NO: 81) |
| JE NS1 | 404-TDLARYVVL-412 (SEQ ID NO: 82) |
| JE Egp | 439-SIGGVFNSIGKAVHQ-455 (SEQ ID NO: 77) |

Preparation of Chimeric T helper anid B Cell Peptides Immunization and Protection Studies T cell epitopes were derived from envelope glycoprotein as their potential to stimulate T cells was earlier checked in our laboratory (Kutubuddin, M, Kolaskar, A S, Salande, S, Gore M M, Ghosh. S N, Banerjee, K. (1991) Recognition of helper T cell epitopes in envelope (E) glycoprotein of Japanese encephalitis West Nile and Dengue virus. Mol. Immunol 28 149-54). It was thus decided to make a synthetic peptide which has both T helper and B cell epitopes in tandem. The peptide that was co-linearly synthesized was:

NH2-SENHGNYSAQVGASQGSIGGVFN-
SIGKAVHQVFG-COOH (SEQ ID NO: 83)

This peptide had two components viz.,

| B cell epitope | 149-SENHGNYSAQVGASQ-163 (SEQ ID NO: 1) |
| --- | --- |
| T cell epitope | 429-SIGGVFNSIGKAVHQVFG-445 (SEQ ID NO: 2) |

The peptide was synthesised as a single peptide co-linearly using solid phase synthesis using FMOC amino acids as mentioned above.

The purified peptide collected as a single peak was lyophilized and used for immunizations. The immunization was done in different strains of adult mice that were both inbred and outbred (n=8). The inbred strains were BALB/C (H-$2^d$) and C3H (H-$2^k$) while the outbred strain was SWISS/Albino. The antigens used for immunization were, the chimeric peptide, B cell peptide, commercial Japanese encephalitis virus vaccine (Obtained from Central Research Institute, Kasauli, India) and PBS (sham). The immunizations were done with a variation in schedule. The immunization schedule was a dose of 50 ug of peptide per mouse per dose through sc route, administered alongwith Freund's adjuvant every 14 days. For the first dose Freund's complete adjuvant while for the subsequent doses incomplete adjuvant was used. A total of two booster doses were given. All the mice were bled through the retro-orbital route on days—3 (preimmune sera), 10, 22, 34 days post first dose. The mice were challenged with a lethal dose of live virus an day 35, which was a week after the last dose. The mice were scored for 21 days post challenge for sickness and death. The immune response was also characterized using usual methods like ELISA, Immunofluorosence assays and virological assays like neutralization and challenge experiments.

Figure 3A:
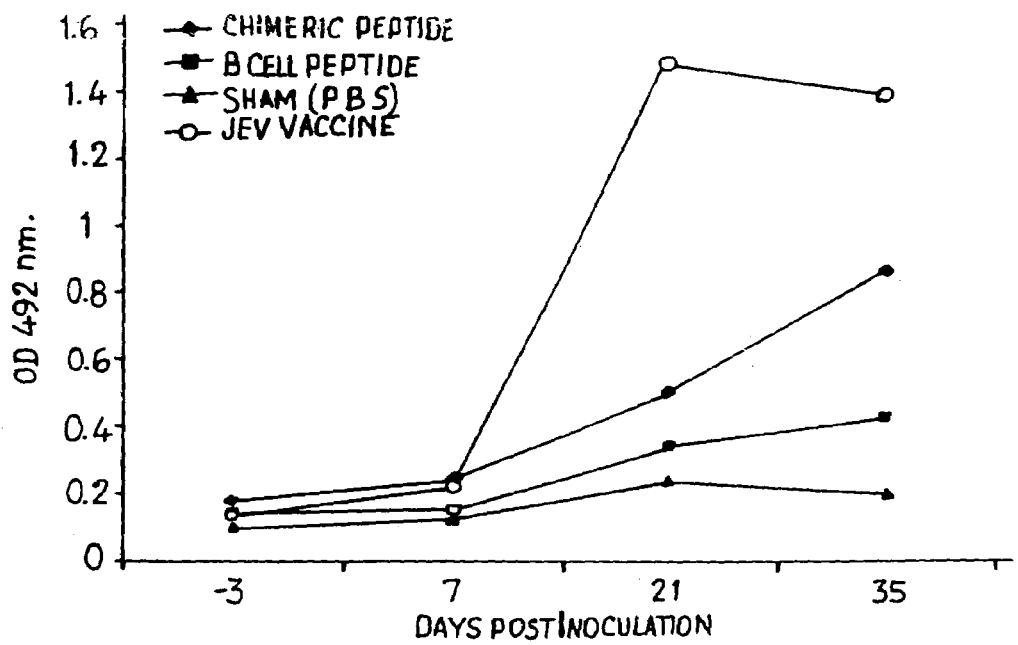
FIG. 3 shows ELISA assays in which anti Japanese encephalitis virus response was tested. It can be seen that the peptides are capable of eliciting immune response against JE virus especially if the chimeric peptide is the immunogen.
Figure 3B:
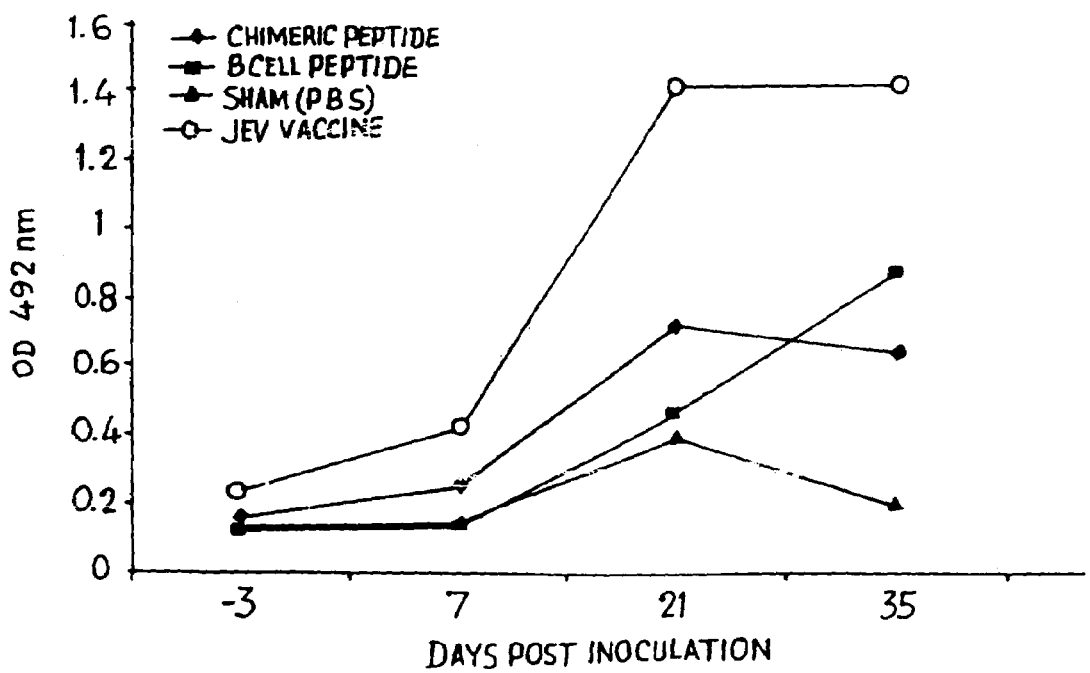
Figure 3C:
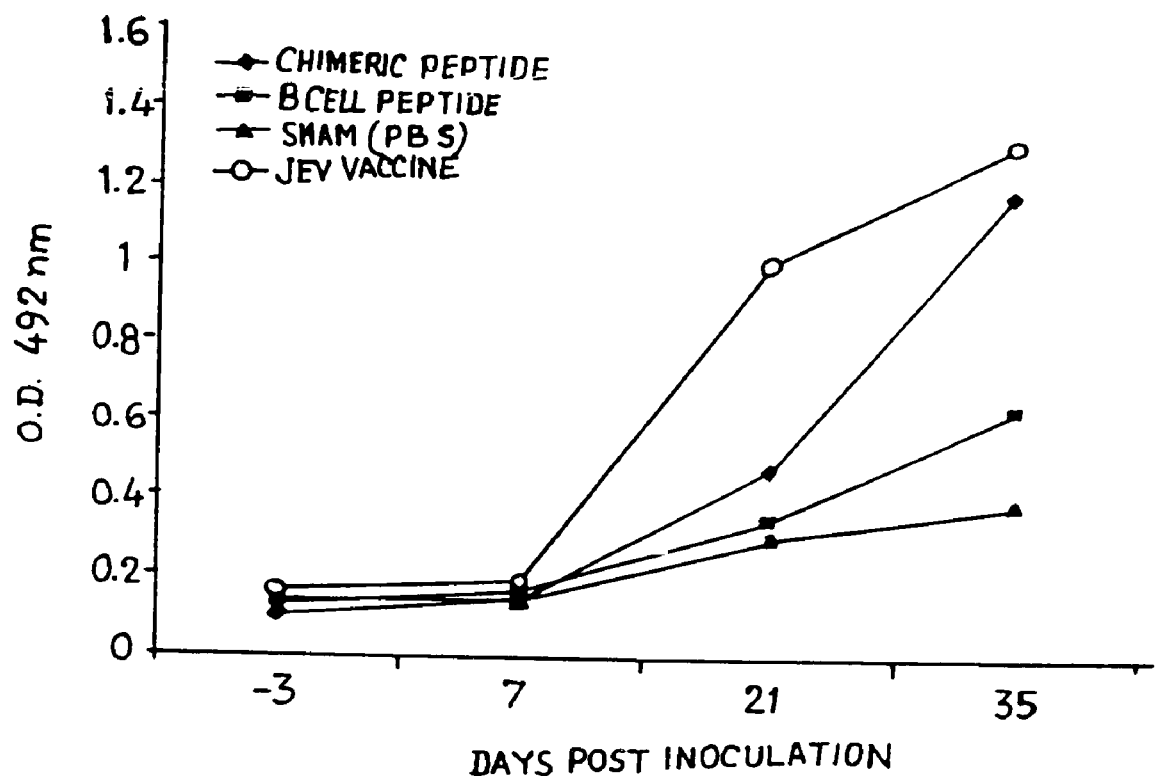

Anti Japanese encephalitis virus response was checked by ELISA. As depicted in the FIGS. 3 a,b,c, it can be seen that the peptides are capable of eliciting immune response against JE virus especially if the chimeric peptide is the immunogen. In terms of immune response, best response was seen in mice immunized with Japanese encephalitis virus vaccine followed by Chimeric peptide and B cell peptide in that order.

Figure 4:
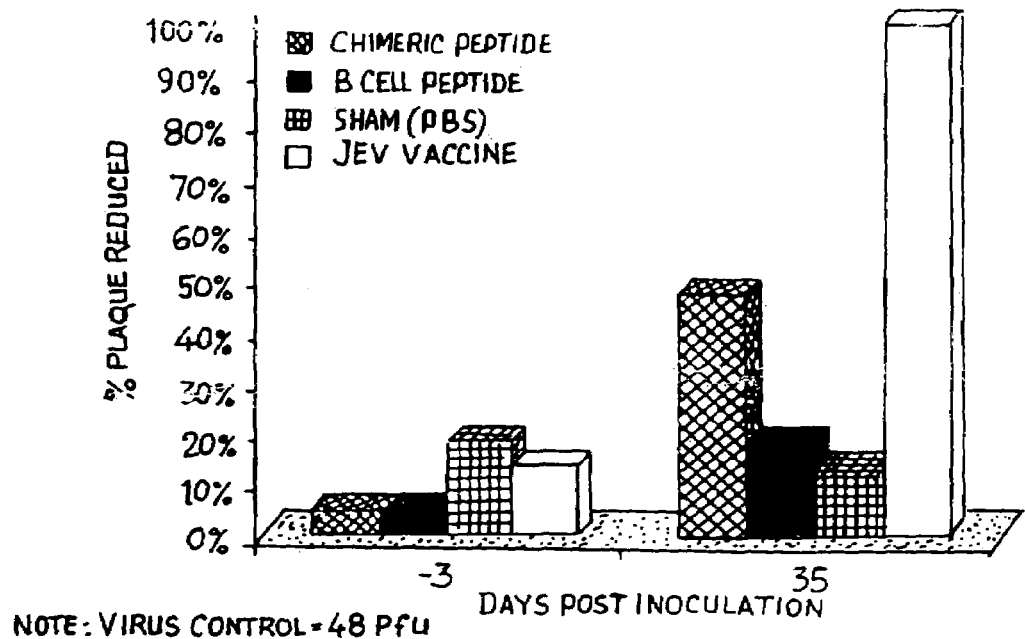
FIG. 4 shows neutralization experiments performed by a plaque reduction assay. In vitro virus neutralization is observed with anti chimeric peptide sera.

In vitro virus neutralization by anti chimeric peptide sera. Neutralization experiments were performed by plaque reduction assay. Antichimeric peptide sera were diluted 1:50 in culture medium. Fifty microliters of the diluted serum and equal volume of virus pool containing 48 plaque forming units were mixed and incubated at 37 C. for one hour. Virus antibody mixture was added on to the preformed Porcine stable kidney cells in 24 well plates. After one hour adsorption caboxymethyl cellulose overlay was added and plates were incubated for 3 days. Percentage plaque inhibition was calculated using virus plaque numbers without antibody. The FIG. 4 shows the efficiency of the anti-peptide sera to neutralize the virus. As seen from the figures only antibodies raised against the chimeric peptides in C3H mice are capable of neutralizing Japanese encephalitis virus.

Protection of Mice Immunized with Chimeric Peptide from Lethal Challenge of Japanese Encephalitis Virus Since the peptides are potential vaccine candidates, the mice immunized were assayed for their ability to resist the virus challenge. Lethal dose of Japanese encephalitis virus was administered according to the protocol by (Yeolekar & Banerjee 1996 Yeolekar, LR and Banerjee, K. (1996) Immunogenicity of immunostimulating complexes of Japanese encephalitis virus in experimental animals. Acta Virologica 40 245-250.). Chimeric peptide immune mice were inoculated intraperitoneally with 0.1 ml Japanese encephalitis virus suspension, immediately followed by inoculation of 0.03 ml of 1% starch solution by intracerebral route. The mice were observed for 21 days post challenge. According to the survival curves in FIG. 5 it can be seen that the C3H mice that were immunized with chimeric peptides were able to resist the virus challenge. The other strains of mice (BALB/c or SWISS) were not able to neutralize the virus nor were they able to resist the virus challenge.

Figure 5:
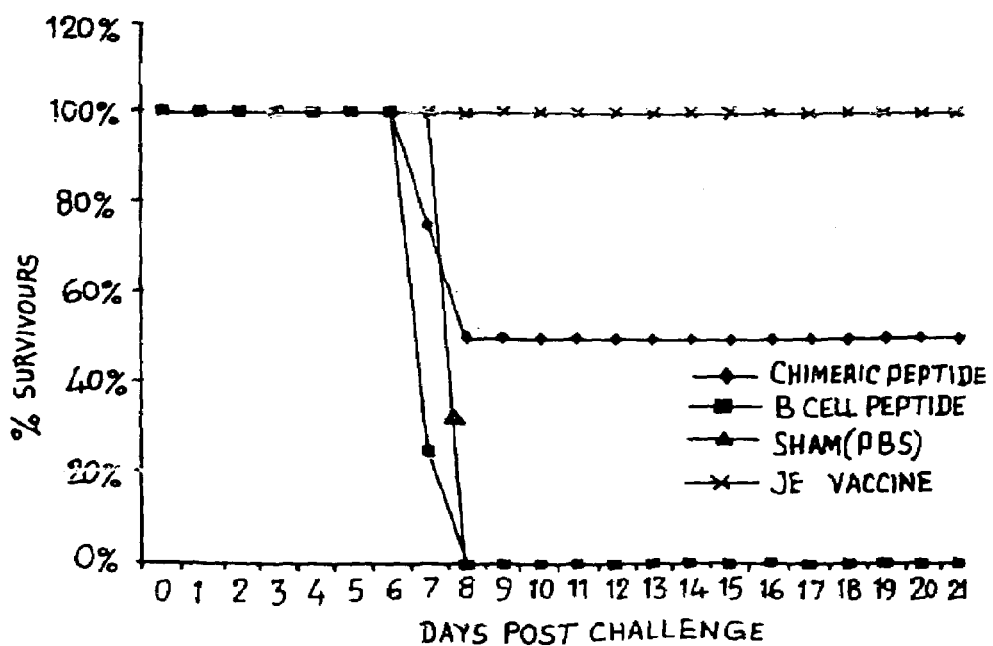
FIG. 5 shows survival curves, which indicate that mice immunized with a chimeric peptide were protected from lethal challenge by Japanese encephalitis virus.

FIG. 5 shows survival of chimeric peptide KK immune mice from Japanese encephalitis virus challenge with a challenge virus dose of 2.3 log LD 50.

The data thus supplied in this document here clearly indicates that it is possible to protect mice from lethal challenge of Japanese encephalitis virus. The data also has been supplied to indicate that in addition to the peptide epitope 149-SENHGNYSAQVGASQAAKF-167 (SEQ ID NO:3) B cell epitopes 39-PTLDVRMINI-48 (SEQ ID NO: 85) and 269-AIVVEYSSSVKLT-281 (SEQ ID NO:86) can also induce neutralizing antibodies to Japanese encephalitis virus and thus are unique. Data has also been presented to indicate that peptides JE Egp 346-HVLGRLTTVN-355 (SEQ ID NO:67), JE 17-EAWLDSTKAT-26 (SEQ ID NO: 68), JE NS1 297-SVRTTTDSGKLITD-310 (SEQ ID NO:71), JE NS1 156-EDFGFGITSTRV-167 (SEQ ID NO:72), JE NS1 404-TDLARVVL-412 (SEQ ID NO:73), JE Egp 439-SIGGVFNSIGKAVHQ-455 (SEQ ID NO:77) can be used as T helper cell peptides. As chimeric T helper B cell peptide has conclusively been shown to protect mice from lethal challenge it is claimed that any or all the combinations of B cell and T helper peptides would be useful in developing vaccine against Japanese encephalitis virus.

We claim:

1. A synthetic polypeptide consisting of a B cell epitope linked to a T-cell epitope, wherein the epitopes are from the Japanese encephalitis virus envelope glycoprotein, and the B cell epitope has the sequence 149-SENHGNYSAQVGASQ-163 (SEQ ID NO:1) and the T cell epitope has the sequence 429-SIGGVFNSIGKAVHQVFG-446 (SEQ ID NO:2).

2. A composition comprising a synthetic polypeptide of claim 1 and a second synthetic polypeptide which consists of a B cell epitope linked to a T cell epitope, wherein the epitopes are from the Japanese encephalitis virus, and wherein the B-cell epitope has a sequence from the envelope glycoprotein, Egp, selected from the group consisting of 149-SENHGNYSAQVGASQ-163 (SEQ ID NO:1), 149-SENHGNYSAQVGASQAAKF-167 (SEQ ID NO:3), 39-PTLDVRMINIEA-50 (SEQ ID NO:4), and 273-EYSSSVKLTSG-283 (SEQ ID NO:5); and the T-cell epitope has a sequence selected from the group consisting of Egp 429-SIGGVFNSIGKAVHQVFG-446 (SEQ ID NO:2), Egp 346-HVLGRLTTVN-355 (SEQ ID NO:67), membrane protein M 17-EAWLDSTKAT-26 (SEQ ID NO:68), nonstructural protein-1 sequences, NS-1 297-SVRTTTDSGKLITD-310 (SEQ ID NO:71), NS-1 156-EDFGFGITSTRV-167 (SEQ ID NO:72), and NS-1 404-TDLARYVVL-412 (SEQ ID NO:73).

3. The composition of claim 2, wherein, in the second synthetic polypeptide, the B-cell epitope has the sequence SENHGNYSAQVGASQ (SEQ ID NO:1), and the T-cell epitope has the sequence SVRTTTDSGKLITD (SEQ ID NO:71).

4. The composition of claim 2, wherein, in the second synthetic polypeptide, the B-cell epitope has the sequence SENHGNYSAQVGASQ (SEQ ID NO:1), and the T-cell epitope has the sequence EAWLDSTKAT (SEQ ID NO:68).

5. The composition of claim 2, wherein, in the second synthetic polypeptide, the B-cell epitope has the sequence PTLDVRMINIEA (SEQ ID NO:4), and the T-cell epitope has the sequence EAWLDSTKAT (SEQ ID NO:68).

6. The composition of claim 2, wherein, in the second synthetic polypeptide, the B-cell epitope has the sequence PTLDVRMINIEA (SEQ ID NO:4), and the T-cell epitope has the sequence SVRTTTDSGKLITD (SEQ ID NO:71).

7. The synthetic polypeptide of claim 1, wherein the B-cell epitope and the T-helper cell epitope are linked by a G residue, and the sequence of the polypeptide is SENHGNYSAQVGASQ G SIGGVFNSIGKAVHQVFG (SEQ ID NO:83).

* * * * *